United States Patent [19]

Andersson et al.

[11] Patent Number: 4,957,485
[45] Date of Patent: Sep. 18, 1990

[54] ARRANGEMENT FOR THE INSTILLATION OF FLUIDS IN A URETHRA

[76] Inventors: Ingvar Andersson, PL 80, S-450 34 Fiskebackskil; Jan Wadstein, Karlavägen 67, S-111 45 Stockholm, both of Sweden

[21] Appl. No.: 313,185
[22] PCT Filed: Aug. 18, 1987
[86] PCT No.: PCT/SE87/00361
§ 371 Date: Feb. 7, 1989
§ 102(e) Date: Feb. 7, 1989
[87] PCT Pub. No.: WO88/01183
PCT Pub. Date: Feb. 25, 1988

[30] Foreign Application Priority Data

Aug. 20, 1986 [SE] Sweden .................................. 8603511

[51] Int. Cl.$^5$ ............................................. A61M 29/00
[52] U.S. Cl. ...................................... 604/96; 604/104; 604/171; 604/176
[58] Field of Search ........................ 604/96, 104–106, 604/171, 181, 174–176, 349–353

[56] References Cited

U.S. PATENT DOCUMENTS 4,419,097 12/1983 Rowland ............................... 604/352
4,810,249 3/1989 Glassman ............................. 604/171

FOREIGN PATENT DOCUMENTS 267597 3/1912 Fed. Rep. of Germany .
3204828 3/1984 Fed. Rep. of Germany .
591191 2/1978 U.S.S.R. ............................... 604/104

*Primary Examiner*—J. L. Kruter
*Attorney, Agent, or Firm*—Jeffers, Hoffman & Niewyk

[57] ABSTRACT

An arrangement for the instillation of fluids in a urethra comprising a tube of rigidity and diameter to be capable of being introduced into the urethra. The invention is characterized in that the length of the tube is a fraction of the length of the urethra, or approximately one decimeter. Along most of its length the tube is executed with an inflatable sac with elastic walls. This exhibits straight cylindrical form in its uninflated state, and in its inflated state has a slim, conical form, the base of which is situated at the end of the tube, and the tip of which is attached to a flange near the other end of the tube. Near the flange the sac has a connection via which the sac can be inflated with and emptied of air. The arrangement also comprises a device adapted to suit the opening of the urethra, made of an elastic material, and anchored to the flange. The device is executed with a connection leading to a vacuum source.

4 Claims, 3 Drawing Sheets

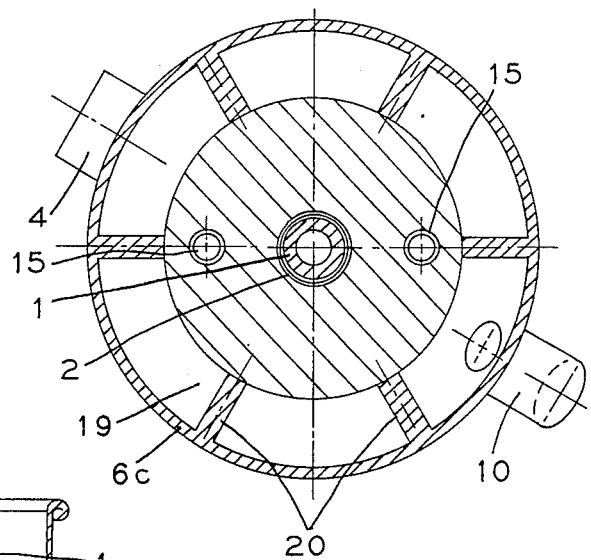
FIG 3b
FIG 3a
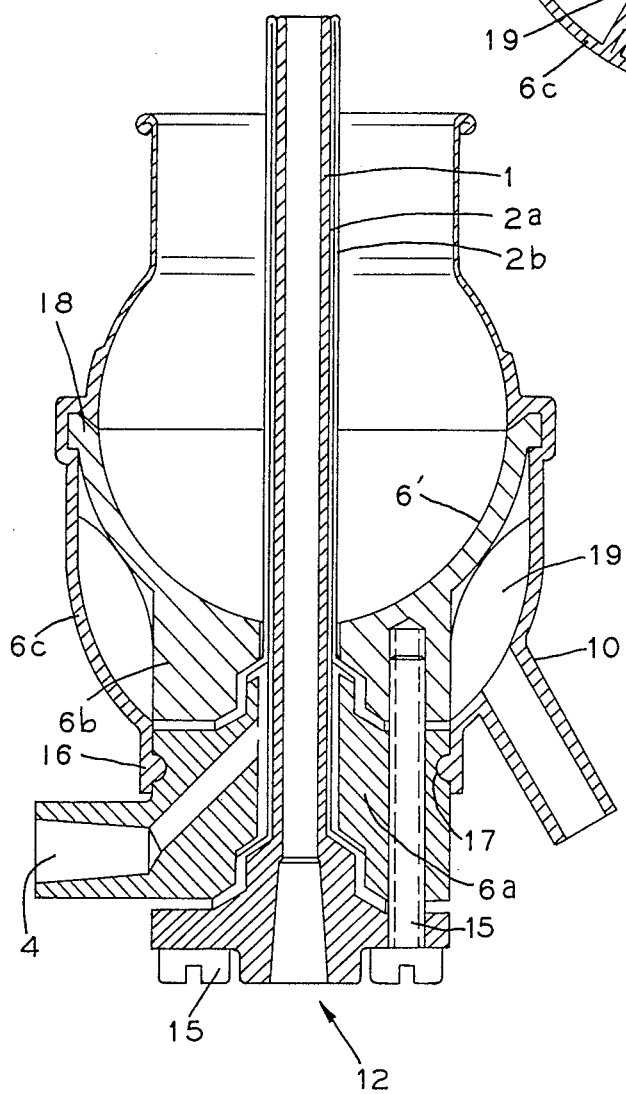

ARRANGEMENT FOR THE INSTILLATION OF FLUIDS IN A URETHRA

BACKGROUND OF THE INVENTION

The present invention related to an arrangement for the instillation of fluids in a urethra comprising a tube of appropriate rigidity and diameter to be capable of being introduced into the urethra, which tube exhibits at its one end a device for the attachment of the tube to a source of the aforementioned fluid.

One disadvantage of previously disclosed instillation arrangements is that it is difficult to achieve a good seal between the opening of the urethra and the instillaton tube. This is unsatisfactory, especially in conjunction with the instillation of cytotoxic drugs, whose leakage can cause harm to the medical and nursing staff.

Furthermore, in previously disclosed installation arrangements, the tube is often so long that, when it has been introduced, it reaches as far as or into the vicinity of the bladder. In this way those bacteria which are normally washed away during urination are able to make their way undisturbed up through the urethra in the space between it and the tube. The result of this is infections, which means that the instillation treatment must be interrupted, to be resumed at a later date once the infection has been arrested, which is unnecessarily painful for the patient and reduces the effectiveness of the treatment.

A further disadvantage associated with the length of the instillation tube in previously disclosed arrangements is the fact that crystals frequently form in the aforementioned space between the instillation tube and the wall of the urethra, against which the crystals chafe, causing pain and a propensity to infection.

SUMMARY OF THE INVENTION

The object of the present invention is to make available an instillation arrangement in which the aforementioned disadvantages have been eliminated, this being made possible in that the length of the tube is a fraction of the length of the urethra, or approximately one decimeter, in that the tube is executed along most of its length with an inflatable sac with elastic walls, which sac exhibits straight cylindrical form in its uninflated state and is so arranged, when in the inflated state, as to adopt a slim, conical form, the base of which is situated at the end of the tube which is intended to be introduced, and the tip of which is attached to a flange anchored to the aforementioned device and in the vicinity thereof is provided with a connection via which the sac can be inflated with and emptied of air, and in that the aforementioned device has a form which is adapted to the opening of the urethra and is executed in a previously disclosed manner with a connection to a vacuum source for the purpose of producing negative pressure at least in an area around the tube.

In accordance with a preferred embodiment of the invention the aforementioned device consists of three parts so arranged as to be operatively connected to one another, of which one part is a base part supporting the tube with its connection, which base part is executed with the connection to the sac and is operatively connected on the one hand to a second part executed with a bowl shaped recess and is manufactured from a rigid, porous and air-permeable material, and on the other hand to a third part which is executed as a thin-walled and generally tubular shell of a flexible material, which, together with the second part forms a chamber communicating with the connection for a vacuum source, the flexible outer wall of which chamber is supported by spacer elements arranged conveniently at mutually identical distances apart or the second part.

In order to provide a good seal with the opening of the urethra without causing pain to the patient, the aforementioned device is executed around the connection to the tube with an annular bowl shaped recess facing towards the end of the tube which is intended to be introduced, in which recess there is arranged a body which fits the form of the recess, which body is made of a porous, air-permeable material with a smooth surface adjacent to the edge of the recess, the intention being, at least occasionally, for the vacuum source to be connected to the recess via the connection.

In order further to increase the certainty of urine not finding its way into the space between the urethra and the instillation arrangement, the external wall of the sac is executed with flanges running all the way round in accordance with one characteristic of the invention.

BRIEF DESCRIPTION OF THE DRAWINGS

FIG. 3a is a longitudinal sectional view of an alternative embodiment of the instillation arrangement.

FIG. 3b is a cross-sectional view of the arrangement shown in FIG. 3a.

Figure 1:
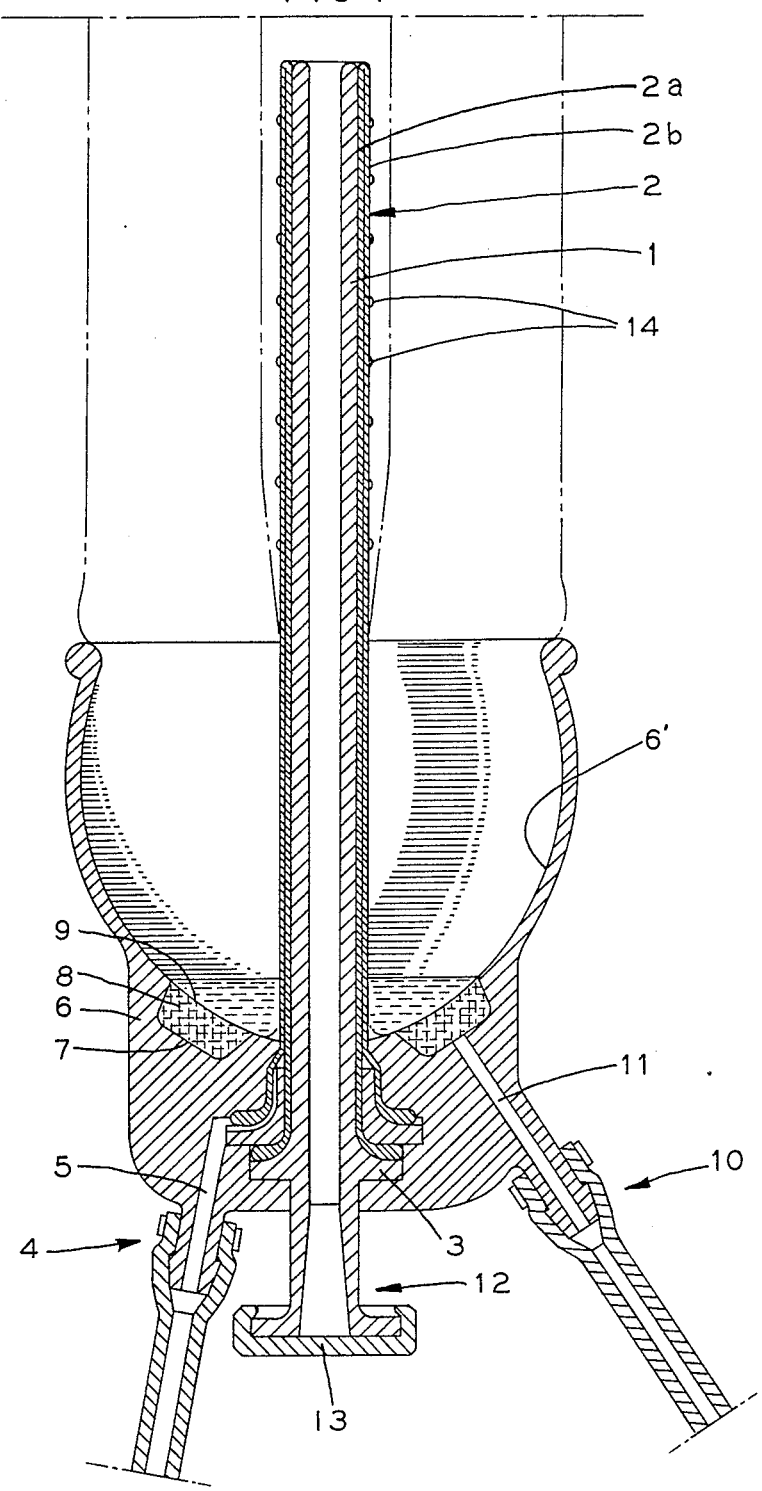
FIG. 1 is a longitudinal sectional view of a preferred embodiment of the instillation arrangement of the present invention, showing the tube introduced into the urethra of a penis.

An instillation arrangement in accordance with the invention comprises a tube 1 of approximately one decimeter in length made of a plastic material which exhibits appropriate rigidity and diameter to be capable of being introduced into a urethra. Along most of its length the tube 1 is executed with an inflatable sac 2 with elastic walls 2a, 2b. In its uninflated state the sac exhibits straight, cylindrical form close against the tube 1 and is so arranged, when in its inflated state, as to adopt a form which fits the urethra, that is to say a slim, conical form, the base of which is situated at the end of the tube which is intended to be introduced, and the tip of which is attached to a flange 3 arranged close to the other end of the tube 1. In the vicinity of the flange 3 the sac 2 is provided with a connection 4, which comunicates via a channel. 5 with the sac 2, and via which the latter can be inflated with and emptied of air.

DESCRIPTION OF THE PREFERRED EMBODIMENT

Anchored to the flange 3 is a device 6, which comprises an adaptation piece, made of a soft, elastic material, for example rubber cr plastic, the form of which is adapted by means of a recess 6" to suit the opening of the urethra and is thus so arranged as to form a tight seal with it. The aforementioned device or adaptation piece 6 is executed around the connection to the tube 1 with a second, annular recess 7 facing towards the end of the tube 1 which is intended to be introduced. Arranged in the latter is an annular body 8 which fits the form of the recess 7 made of a porous, air-permeable material, for example felt or ceramic. The surface 9 of the body 8 which faces towards the end which is intended to be introduced is smooth and lies flush with the edge of the recess 7, and in other respects follows the form adapted to suit the opening of the urethra. A connection 10 communicates via a channel 11 with the recess 7. The connection 10 is intended to be connected to a vacuum source not shown in the drawing.

The aforementioned other end of the tube 1 is executed with a connection 12 for a hypodermic syringe or similar, which connection 12 is conveniently executed as a so-called Luer cone. In FIG. 1 this connection is protected by a cover 13.

In order to provide the best possible seal between the wall of the urethra and the external wall 2b of the sac 2, this is executed with radial flanges 14 running all the way round.

The embodiment of the instillation arrangement in accordance with the invention illustrated in FIG. 3, in respect of which the previously used references have been applied to components having the same or a similar function, differs from the embodiment described above primarily in that it is composed of three coacting parts 6a, 6b, 6c. The part 6a is a base which supports the tube 1 with its connection 12 and the parts 6b and 6c, and is executed with a connection 4 for the sac 2 in the same way as previously described. The part 6b, which is secured by means of screws 15 to the base part 6a exhibits a recess 6" in the same manner as the adaptation piece 6 and is manufactured from a rigid, porous and air-permeable material, for example the same material as is used in the annular body 8 referred to above. The part 6c is executed as a thin-walled, generally tubular shell, the walls of which are thin and are made of a flexible material such as rubber. One end of the tubular part is in engagement by means of an internal bead 16 with a corresponding groove 17 arranged in the base part 6a, immediately above the connection 4, and approximately at its centre the tubular part 6c is so arranged as to engage with a projecting flange 18 running around the external periphery of the part 6b. The part 6c is otherwise executed in a similar manner to the adaptation piece 6 illustrated in FIG. 1. Between the flange 18 and the bead 16 the parts 6b and 6c define a chamber 19 which communicates with a connection 10 for the purpose of its connection to a vacuum source. Projecting outwards from the part 6c are radial flanges 20, arranged conveniently at mutually identical distances apart and so executed as to support the chamber wall, in particular when the chamber 19 is under negative pressure, in conjunction with which the chamber wall bends inwards. The chamber 19 then acts as a vacuum reserve with the job of compensating for any leakage. An experienced observer can estimate the level of negative pressure from the inward deflection of the wall.

Figure 2:
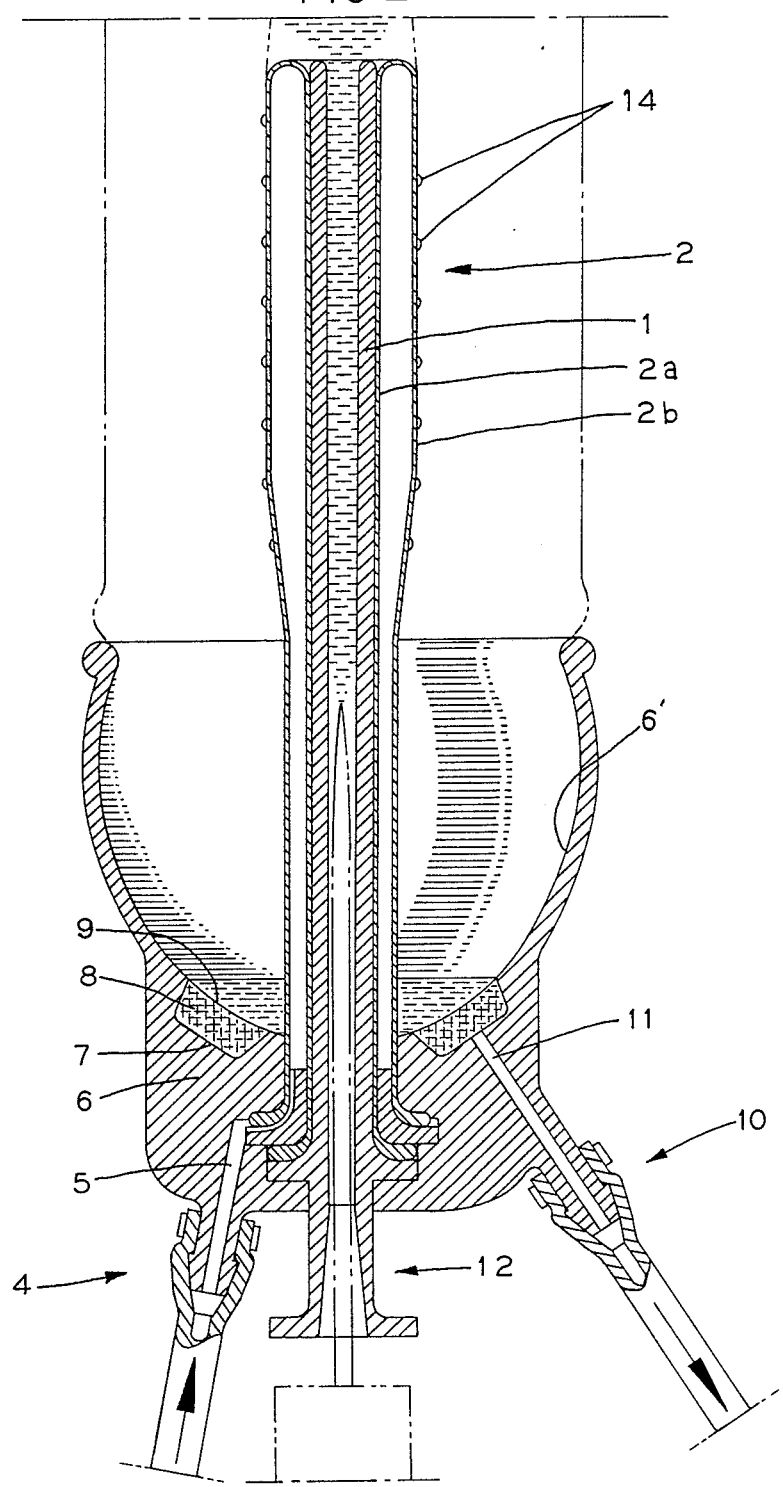
FIG. 2 is a longitudinal sectional of the embodiment shown in FIG. 1, showing the sac in its inflated state.

When using the arrangement in accordance with the invention, the tube 1 with the sac 2 is introduced into the urethra for a distance such that the internal space of the adaptation piece 6 which is shaped to fit the opening of the urethra fits flush against the aforementioned opening. The connections 4 and 10 are then attached to a source of pressurized air, for example an air pump, and to a vacuum source. A sufficient quantity of air is pumped into the sac from the source of pressurized air to cause it to adopt the form illustrated in FIG. 2. In this way a reliable seal is produced between the tube 1 and the wall of the urethra. By means of the connection to the vacuum source secure fixing of the arrangement is achieved without discomfort to the patient.

We claim:

1. An arrangement for the instillation of fluid in a urethra comprising:
   a tube connected to a source of fluid for instillation into the urethra, said tube having sufficient rigidity and diameter for insertion into the urethra, said tube having two ends, one end of said tube being adapted for insertion into the urethra, the other end of said tube being adapted to remain outside of said urethra and having a flange positioned thereon, said tube having a length of about one decimeter;
   an inflatable sac engaging the outer surface of said tube and extending from said one end of the tube substantially the length of said tube toward said other tube end, said sac having elastic walls and having respective inflated and uninflated conditions, said sac having a generally cylindrical configuration when in its uninflated condition and having a generally conical configuration when in its inflated condition, said generally conical configuration comprising a base situated at said one end of the tube and a tip situated generally at said flange at said other end of the tube;
   an adaptation piece positioned at said other end of the tube and having said flange anchored therein, said adaptation piece having a form adapted to the opening of the urethra and being aligned with said urethra so that said tube extends from said adaptation piece into said urethra;
   means in fluid communication with said sac for connecting said sac with a source of air, whereby said sac may be inflated with and emptied of air; and
   means in fluid communication with said adaptation piece for connecting said adaptation piece to a vacuum source for producing negative pressure between said adaptation piece and said urethra.

2. The arrangement of claim 1, in which said adaptation piece comprises a first part, a second part and a third part, said first part comprising a base for supporting said tube and for supporting a connection portion situated between said tube and a source of said fluid; said second part being formed of a rigid, porous and air-permeable material and being operatively connected with said first part, said second part further having a bowl-shaped recess formed therein; said third part having a thin-walled generally tubular shell formed from a flexible material and being operatively connected with said first part; said second part and said third part forming a chamber wherein said thin-walled generally tubular shell comprises a flexible outer wall of said chamber, and wherein a plurality of spacer elements are positioned in said chamber between said second part and said third part for supporting said flexible outer shell.

3. The arrangement of claim 1, wherein said adaptation piece has an annular recess formed therein and extending inwardly from an outer surface of said adaptation piece, said annular recess bring situated so that it surrounds said tube and faces said end of the tube adapted to be inserted into the urethra, said annular recess having an annular body positioned therein, said annular body being formed of a porous, air-permeable material having a smooth outer surface, said smooth outer surface being aligned with the outer surface of the adaptation piece, and being located adjacent said outer surface, said annular recess being in communication with said means for connecting said adaptation piece to a vacuum source.

4. The arrangement of claim 1, in which said sac has an external wall, said external wall having a plurality of flanges extending circumferentially around said external wall.

* * * * *